United States Patent [19]

Siegers et al.

[11] Patent Number: 4,708,900

[45] Date of Patent: Nov. 24, 1987

[54] FIBROUS PERFUME CARRIER FOR ARTIFICIAL FLOWERS AND A PROCESS FOR ITS MANUFACTURE

[75] Inventors: Hans-Peter Siegers, Wegberg; Wilfried Macke, Toenisvorst, both of Fed. Rep. of Germany

[73] Assignee: Henkel Kommanditgesellschaft auf Aktien, Duesseldorf, Fed. Rep. of Germany

[21] Appl. No.: 719,176

[22] Filed: Apr. 3, 1985

[30] Foreign Application Priority Data

Apr. 30, 1984 [DE] Fed. Rep. of Germany ....... 3416007

[51] Int. Cl.⁴ .................. B32B 5/02; A41G 1/00; D04H 11/04
[52] U.S. Cl. .................................. 428/74; 264/116; 264/137; 264/154; 264/257; 422/120; 428/17; 428/24; 428/542.8; 428/905
[58] Field of Search ............... 264/137, 154, 116, 257; 428/17, 24, 74, 542.8, 905; 422/120, 125, 122

[56] References Cited

U.S. PATENT DOCUMENTS

| | | | |
|---|---|---|---|
| 2,141,402 | 12/1938 | Muller | 428/24 X |
| 2,249,888 | 7/1941 | Dodge | 264/257 X |
| 2,378,642 | 6/1945 | Kopplin | 264/137 |
| 2,963,744 | 12/1960 | Cooper | 264/137 X |
| 3,567,119 | 3/1971 | Wilbert | 428/17 X |

FOREIGN PATENT DOCUMENTS

| | | |
|---|---|---|
| 8212730 | 9/1982 | Fed. Rep. of Germany . |
| 50-28868 | 9/1975 | Japan ..................................... 428/24 |

Primary Examiner—Philip Anderson
Attorney, Agent, or Firm—Ernest G. Szoke; Henry E. Millson, Jr.; Mark A. Greenfield

[57] ABSTRACT

To provide the perfume carrier of an artificial flower both with a high absorption capacity and with high mechanical stability, a random-fiber fleece of rayon staple fibers is mechanically stabilized by needle punching and then compressed in a press of which all the forming surfaces are heated.

33 Claims, 16 Drawing Figures

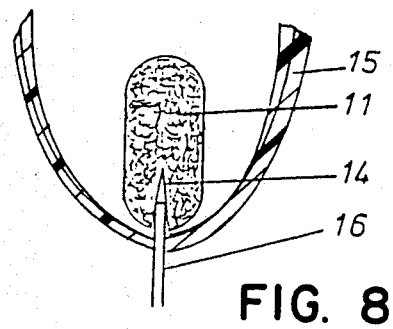
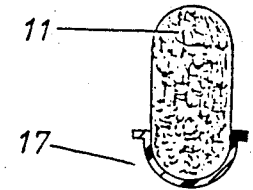
FIG. 8  FIG. 9
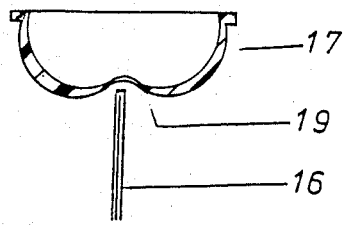
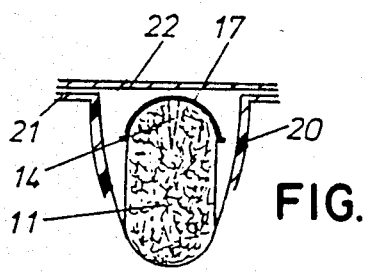
FIG. 10
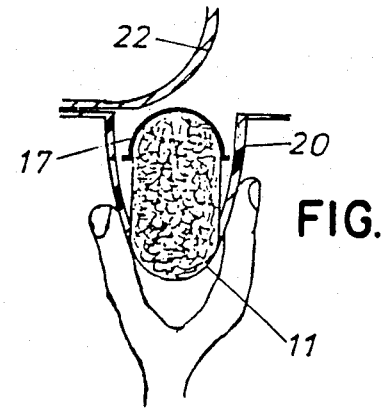
FIG. 11  FIG. 12
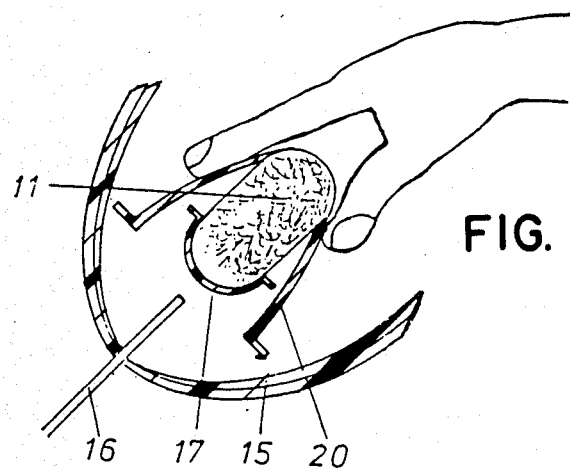
FIG. 13

FIBROUS PERFUME CARRIER FOR ARTIFICIAL FLOWERS AND A PROCESS FOR ITS MANUFACTURE

BACKGROUND OF THE INVENTION

1. Field of the Invention

This invention relates to a method of making a perfume carrier for a perfumed artificial flower consisting of an absorbent material, such as a nonwoven, with a surface which releases the perfume by evaporation. The invention also relates to a perfume carrier made by this method and to its perfume cartridge.

2. Statement of Related Art

An artificial flower having a perfume reservoir is described in German Utility Model No. 82 12 730.1 and corresponding pending U.S. patent application Ser. No. 06/489,833 filed Apr. 29, 1983 and now abandoned. This known artificial flower is said to simulate the smell of fresh flowers either on its own or as part of a bouquet of artificial flowers and to give off a correspondingly pleasant fragrance to the surrounding atmosphere. Since artificial flowers with their almost life-like appearance tend to keep for a long time, efforts are continually being made to counteract the relatively rapid fading of the perfume. Accordingly, it is proposed in German Utility Model No. 82 12 730.1 releasably to attach a perfume wick of a highly absorbent material charged with the particular perfume to a support arranged in the cup of the artificial flower. When the perfuming effect of the wick weakens, a new perfume wick, i.e. a new perfume reservoir, can be introduced into the flower.

The known perfume wick may consist of a soft absorbent nonwoven and may have a color corresponding to the flower. The insertion of the perfume wick into the particular artificial flower is made easier if a disc having a spike directed vertically outwards for piercing the wick is used as the support in the flower cup. Finally, German Utility Model No. 82 12 730.1 states it to be of advantage to fix that end of the perfume wick facing the support in a flat plastic container of which the base—when used to clamp the fastening of the perfume wick—can be pierced by the spike.

Problems arise during the production, filling and packing of the known perfume wick because a high level of absorbency is required without the surface of the perfume carrier appearing wet and also because high axial stability and firm anchorage coupled with easy fitting are required. The absorption capacity must be high to enable the perfume carrier, despite its very small volume, to take up a large amount of perfume for prolonged use. High axial stability is required to ensure that the perfume carrier retains its shape when fitted and removed.

Known nonwovens of cellulose fibers are highly absorbent but show unsatisfactory stability. The dimensional stability of these fibers cannot be increased for the application in question even by using binders or by high-temperature consolidation after the addition of synthetic fibers because—quite apart from the higher costs involved—this would reduce absorbency and hence useful life.

SUMMARY OF THE INVENTION

The present invention provides a method of making a perfume carrier by which maximal absorbency and, at the same time, sufficient axial stability for handling are obtained. According to the invention, this is achieved in that a nonwoven of rayon staple fibers is mechanically stabilized by needle punching and in that the stabilized fibrous blank is compressed in a press of which all the forming surfaces are heated. The perfume carrier according to the invention is characterized by a rayon staple fiber pressing with a compression of less than 0.6 g/cc and a perfume holding capacity of at least 0.4 g/cc.

The raw material used for producing the perfume carrier according to the invention is preferably rayon staple having a denier of approx. 3.6 dtex and a staple length of the order of 30 mm. The fibers may be colored with oil- and water-resistant dye to match the color of the flowers. Where suitably large quantities of fiber are used, it is even possible to use spinneret-dyed rayon staple.

Processing of the fibers into a nonwoven having, for example, a weight per unit area of 600 g/m$^2$ is preferably carried out on a random-fiber fleece production line. To lighten the colors, the fibers may even be blended with white fibers, preferably in a fixed ratio. The fibers are opened in one or more opening units and laid to form a fleece on a pneumatically depositing random-fiber card. The fleece thus formed is then mechanically stabilized in a needle punching machine. Needle punching imparts above all the stability required for fitting and removal of the perfume carrier. Accordingly, binders and/or thermal consolidation (after the addition of synthetic fibers) are unnecessary for mechanical stabilization.

After needle punching, the nonwoven is preferably cut into pieces measuring 30×40 mm and fed to a jaw press. During the pressing operation, the nonwoven folds in the jaw press, typically in the form of a W, giving a radially compressed round fibrous blank. The jaw press may be heated to reduce the fiber-on-metal friction.

After the jaw press, the fibrous blank passes into a heated press cylinder. It may be pushed by means of a push rod from the jaw press into the press cylinder and axially compressed therein, the fibrous blank being adapted in its shape to the contour of the press sleeve and ram. A clean, stable form of the perfume carrier is only obtained if all the surfaces of the press, including the head closure and the ram, are heated. After the head closure and the ram of the press cylinder have returned, the perfume carrier is preferably left in the press sleeve for a short time, for example for about 8 to 15 seconds.

Preparation of the fibrous blank and the subsequent pressing operation are regulated in such a way that the perfume carrier receives a specific compression of less than 0.6 g/cc, so that at least 0.4 g/cc of perfume can be taken up without the surface of the carrier appearing wet. This is achieved, along with the necessary mechanical stability, providing the fleece is first opened, deposited and needle-punched, initially compressed and finally compressed under heat in the manner described above.

The dimensional accuracy of a fibrous pressing or perfume carrier made in this way is naturally not very high, but since high dimensional accuracy is required for mechanical handling and for reproducible fixing in the artificial flower, it can be of advantage to insert the perfume carrier into a plastic bowl of which the diameter should be gauged to enable the perfume carrier to be held by clamping. In the bottom of the bowl, there should be, preferably, clamping lips which should surround a wire projecting from the plastic flower, particularly into the flower cup, with a predetermined holding force after fitting and closing. The shape of the bowl may be similar to that of the inner petals or stamen. Like the fibers, the plastic used must of course be resistant to the perfume itself, i.e. generally water- and oil-resistant.

The perfume carrier has to be packed in diffusion-resistant form pending use. According to another aspect of the invention, a cartridge is used both for charging the perfume carrier with perfume and also as an aid for inserting the perfume-filled carrier into the appropriate place in the particular artificial flower. To form such a cartridge, the perfume carrier is introduced with its head end at the front into a plastic beaker containing liquid perfume. The perfume carrier takes up the perfume, in most cases immediately. After introduction of the perfume carrier, the beaker is sealed with a diffusion-resistant foil, preferably an aluminium foil.

When the perfume carrier is inserted into an artificial flower, the cartridge can serve as a finger guard by preventing the fingers from being wetted with perfume. To this end, the cartridge may be designed as a peel-off cartridge or as a pierce-open cartridge. In the first case, the cover foil is first pulled off, after which the beaker—held between the fingers—is introduced into the flower cup and anchored in a clamp or the like provided there. In the second case, the foil covering the beaker is pierced by the wire or the like holding the artificial flower and the perfume carrier pushed in until the clamp mechanism of the flower is activated. Thereafter the cartridge is withdrawn, tearing open the foil, so that the perfume carrier remains behind in the flower.

BRIEF DESCRIPTION OF THE DRAWINGS

Details of the invention will now be described with reference to examples of embodiments diagrammatically illustrated in the accompanying drawings, wherein:

FIG. 8 shows a perfume carrier fixed in a flower cup.

FIG. 9 shows a perfume carrier with a bowl held thereon.

FIG. 10 shows a bowl and the associated insertion funnel in cross-section (10A) and in elevation (10B).

FIG. 11 is a cross-section through a perfume carrier in a diffusion-resistant cartridge.

FIGS. 12 and 13 show a peel-off cartridge corresponding to FIG. 11 during the manipulation by which the perfume carrier is placed on a holder in an artificial flower.

DETAILED DESCRIPTION OF THE INVENTION

Figure 1:
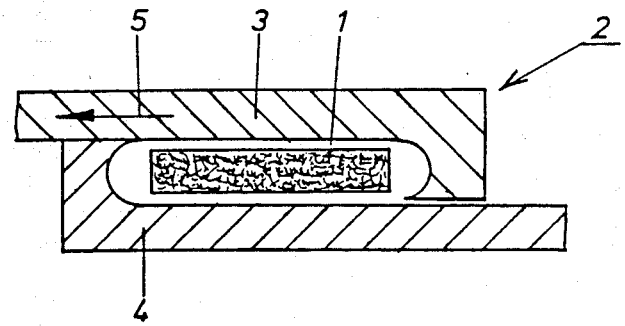
FIGS. 1 to 3 show the pressing of a piece of nonwoven in a jaw press.
Figure 2:
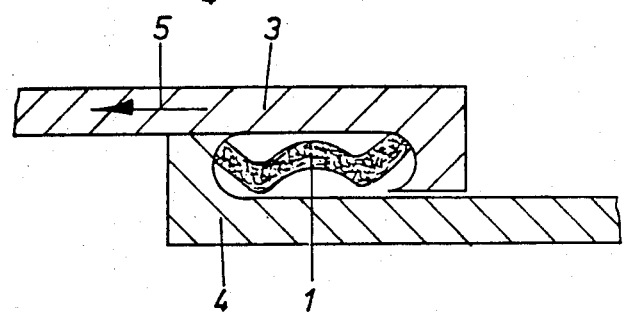
Figure 3:
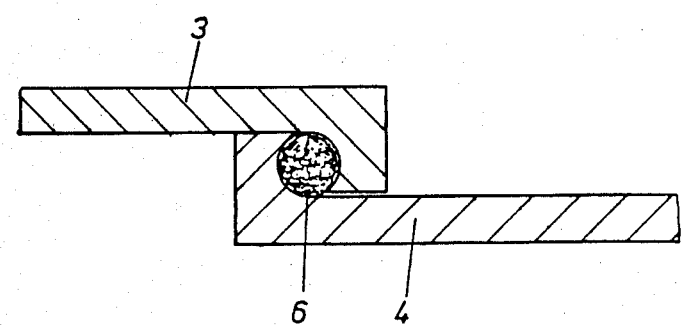

As shown in FIGS. 1 to 3, a section 1 of a nonwoven consisting of rayon staple fibers and coming from a random-fiber card is first folded in the shape of a W in a jaw press 2 by displacement of the jaws 3 and 4 towards one another in the direction of the arrow 5 and, finally, is radially compressed to form a round fibrous pressing 6.

Figure 4:
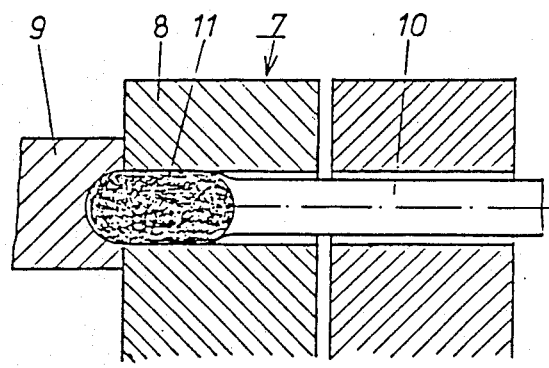
FIGS. 4 and 5 show the pressing of the fibrous blank, initially compressed as shown in FIGS. 1 to 3, in a heated press cylinder.
Figure 5:
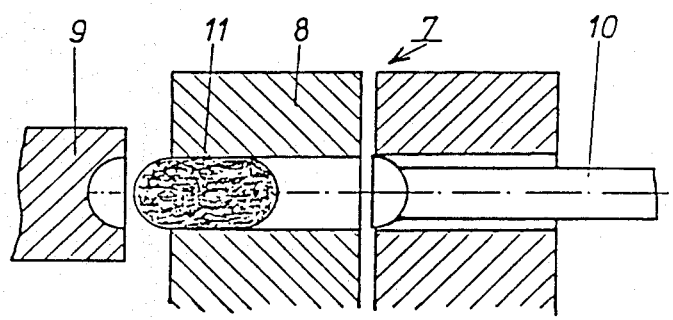

The fibrous pressing 6 is pushed from the jaw press 2, for example by means of a push rod, into a heated press cylinder generally denoted by the reference 7 (cf. FIGS. 4 and 5) and axially compressed. In the press cylinder 7, the fibrous blank is adapted in its external form to the contours of the press sleeve 8, the head closure 9 and the ram 10. A clean stable formed perfume carrier 11 thus produced is only obtained if all the surfaces of the press cylinder 7, including the head closure 9 and the ram 10, are heated. After the head closure 9 and the ram 10 have been withdrawn, the finished perfume carrier 11 should be left in the heated press sleeve 8 for a short time, preferably for 8 to 15 seconds.

Figure 6:
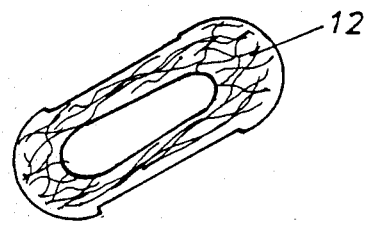
FIGS. 6 and 7 shows examples of external forms of the pressed perfume carrier.
Figure 7:
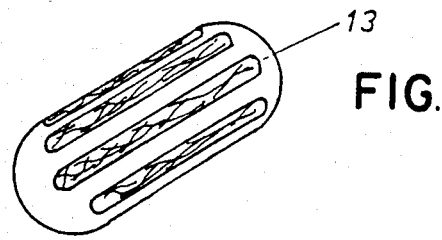

During the forming operation in the press cylinder 7, the perfume carrier 11 may be given a contour 12 similar to a natural flower stamen, as shown in FIG. 6. The contour may correspond generally to that of the natural flower upon which the artificial flower in which it inserted has been modeled. In addition, it can be of advantage to impress grooves 13 (cf. FIG. 7) in the evaporating surface of the perfume carrier 11 by correspondingly grooving the surface of the press cylinder 7. Finally, the perfume carrier 11 may be formed with an indentation or appendage for fastening in the particular artificial flower. FIG. 8 shows, for example, a perfume carrier 11 with a hole 14 tapering to a point at its lower end, into which a wire 16 provided in the flower cup 15 may be inserted for fastening the perfume carrier.

Since the perfume carrier 11 in the form of a fibrous pressing does not of course have any significant dimensional accuracy, it can be of advantage, so far as mechanical handling is concerned, to insert the perfume carrier into a plastic bowl 17 (cf. FIG. 9). The diameter of the bowl should be gauged in such a way that the perfume carrier 11 is held in the bowl 17 by clamping. As shown in FIG. 10, clamping lips 18 may be provided on the bottom of the bowl, optionally surrounding the wire 16 present in the artificial flower with a predetermined holding force. Finally, it can be of advantage, as shown in FIG. 10, to provide an insertion funnel 19 in the base of the bowl 17 to make it easier to place the perfume carrier on the particular holding wire 16 of the artificial flower.

Since the perfume carrier is of course designed to release the perfume, it has to be packed in diffusion-resistant form pending its actual use. According to another aspect of the invention, a cartridge holding the carrier is designed not only to prevent diffusion, but also for charging the perfume carrier with the perfume and, at the same time, as an aid to the insertion of the perfume carrier into an artificial flower.

A diffusion-resistant cartridge, which in addition should consist of water- and oil-resistant material, may be made by heat-forming or welding. The surfaces to be welded should not be wetted with the perfume. The cartridge preferably used is a deep-drawn beaker 20 of acrylonitrile-methyl methacrylate (AMMA) copolymer film.

In practice, the liquid perfume may be introduced into the beaker 20 in the actual deep-drawing machine. In this way, the surfaces to be welded are prevented from being wetted at the rim 21 of the beaker. In the next step, the perfume carrier 11 with its head end to the front is introduced into the beaker 20. The perfume carrier takes up the perfume immediately. Immediately after the perfume carrier 11 has been inserted, the beaker 20 is sealed with a diffusion-resistant foil 22, preferably an aluminium foil. The sealed beaker may optionally be punched out from a sheet of foil in the usual way.

Figure 14:
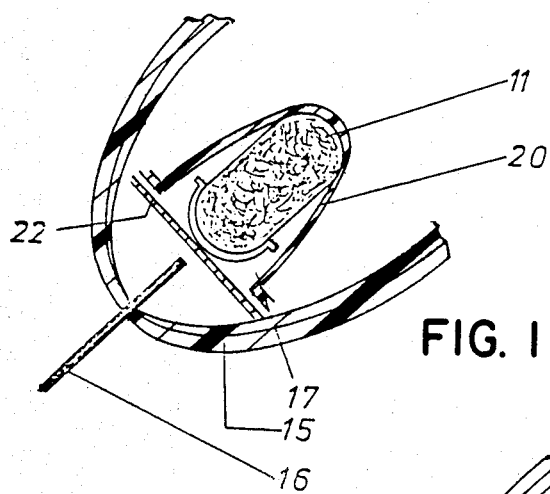
FIGS. 14 to 16 show a pierce-open cartridge corresponding to FIG. 11 during the manipulation by which the perfume carrier is fastened to the holder of an artificial flower.
Figure 15:
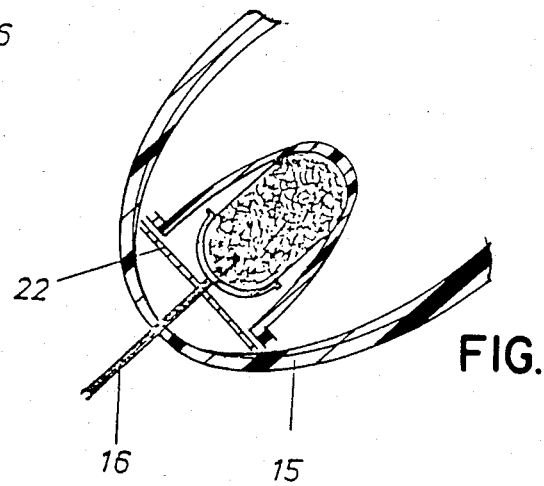
Figure 16:
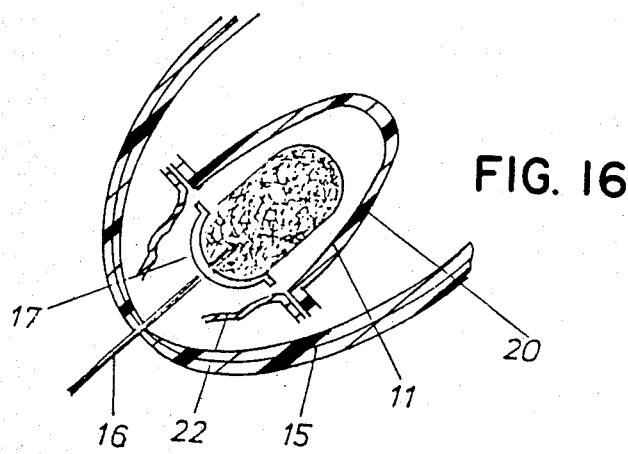

When the perfume carrier 11 is introduced into the flower cup 15 of an artificial flower, the beaker 20 serves as a finger guard. This beaker-shaped pack may be designed and used either as a peel-off pack as shown in FIGS. 12 and 13 or as a pierce-open pack as shown in FIGS. 14 to 16.

Where it is a peel-off pack, as shown in FIGS. 12 and 13, the cover foil 22 is first pulled off, after which the perfume carrier 11—held between the fingers in the beaker 20—is inserted into the flower cup 15 and pushed onto the holder in the form of a wire 16 in the embodiment in question. The beaker-shaped pack may then be withdrawn from the flower cup 15. When the pack is in the form of a pierce-open pack, the cover foil 22 is pierced by the holding wire 16 of the artificial flower, as shown in FIGS. 14 and 15. The perfume carrier 11 is then pushed into the flower cup 15 until the holding mechanism, for example the holding of the wire 16 in the hole 14 (cf. FIG. 8), is activated. The beaker-shaped pack is then withdrawn, tearing the foil 22 open, so that the perfume carrier remains, optionally held, in the plastic bowl 17 (cf. FIG. 16).

We claim:

1. A method of manufacturing a perfume carrier for an artificial flower consisting essentially of:
   mechanically stabilizing a nonwoven absorbent material having a surface which releases the perfume by evaporation, by needle punching said nonwoven; and
   axially compressing said stabilized nonwoven in a cylindrical ram press of which all surfaces contacting said nonwoven are heated, until a perfume carrier blank is formed.

2. A method of manufacturing a perfume carrier blank for an artificial stemmed flower comprising the sequential steps of:
   (a) opening rayon staple fibers in an opening unit and then depositing them to form a fleece in a pneumatically depositing random-fiber fleece card;
   (b) mechanically stabilizing the fleece on a needle punching machine to form a nonwoven;
   (c) cutting the nonwoven into pieces and compressing the pieces in a jaw press to form a radially compressed round fibrous blank;
   (d) pushing said fibrous blank by means of a push rod, into a cylindrical ram press cylinder heated on all sides and axially pressing it therein; and
   (e) leaving the fibrous perfume carrier blank thus formed in said press cylinder for a short period after withdrawal of the ram.

3. The method of claim 2 wherein said fibers are colored with an oil and water resistant dye matching the color of said artificial flower.

4. The method of claim 2 wherein said fibers are colored with an oil and water resistant dye matching the color of said artificial flower, prior to step (a).

5. The method of claim 2 wherein said rayon fibers have a denier of about 3.6 dtex and a staple length of about 30 mm.

6. The method of claim 2, wherein a fleece having a weight per unit area of around 600 g/m² is deposited by said random fiber fleece card.

7. The method of claim 2, wherein the nonwoven is cut into pieces measuring about 30×40 mm before it is delivered to the jaw press.

8. The method of claim 2, wherein said compressed perfume carrier blank is left in said press cylinder for about 8 to 15 seconds.

9. The method of claim 2, wherein said jaw press is heated so as to reduce the fiber-on-metal friction.

10. The method of claim 2, wherein the specific compression of the fibrous pressing to be used as the perfume carrier is limited to a value of less than about 0.6 g/cc.

11. The method of claim 2, wherein the fibrous pressing to be used as the perfume carrier is formed with an indentation in the form of a hole, for the insertion of a wire projecting from the particular flower.

12. The method of claim 2 wherein the fibrous pressing to be used as the perfume carrier is inserted at its rear end into an elastic and oil-resistant plastic bowl serving as an adapter for fastening in an artificial flower.

13. The method of claim 2 wherein the fibrous pressing to be used as the perfume carrier is inserted with its head end at the front into a beaker of diffusion-resistant material containing liquid perfume and wherein the beaker is then sealed against diffusion with a foil.

14. The method of claim 13, wherein the beaker is used as a finger guard when the perfume carrier is being inserted into an artificial flower.

15. A perfume carrier blank manufactured by the method of claim 1.

16. A perfume blank for an artificial flower, manufactured from rayon staple fibers by the method of claim 2, said blank having a specific compression of less than about 0.6 g/cc and a perfume holding capacity of at least 0.4 g/cc.

17. A perfume blank for an artificial flower according to claim 16, wherein said rayon staple fibers have a denier of about 3.6 dtex and a staple length of about 30 mm.

18. The perfume carrier blank of claim 16 having the general contour of the stamen of a natural flower upon which said artificial flower has been modeled.

19. The perfume carrier blank of claim 17 having the general contour of the stamen of a natural flower upon which said artificial flower has been modeled.

20. The perfume carrier blank of claim 18 having a surface area enlarged by means of grooving.

21. The perfume carrier blank of claim 19 having a surface area enlarged by means of grooving.

22. The perfume blank of claim 21 having means for fastening it to a portion of the protruding stem of an artificial flower.

23. The perfume carrier blank of claim 22 wherein said means is a hole in one end of said blank which ends in a conical taper and which is adapted to receive and fasten to said protruding stem portion.

24. The perfume carrier blank of claim 22 wherein said means is a bowl clamped to and capping one end of said blank and which is adapted to receive and fasten to said protruding stem portion.

25. The perfume carrier blank of claim 24 wherein said bowl comprises an elastic and oil resistant plastic capable of being pierced by said protruding stem portion.

26. The perfume carrier blank of claim 24 wherein said bowl comprises an elastic and oil resistant plastic having a hole edged by clamping lips at its center, adapted to receive and fasten to said protruding stem portion by the biasing of said lips against said stem.

27. The perfume carrier blank of claim 26, wherein said bowl is inwardly indented at its center, so that said protruding stem is guided to said hole.

28. The combination of the blank of claim 16 and a sealed cartridge, wherein said blank is enclosed in said sealed cartridge which also contains a perfume suitable to the artificial flower to which it is to be attached.

29. The combination of claim 28 wherein said cartridge comprises a beaker of a depth sufficient to completely enclose said blank and a foil cover sealing the mouth of said beaker.

30. The combination of claim 29 wherein said beaker is comprised of a deep-drawn acrylonitrile-methylmethacrylate copolymer film and said foil comprises aluminum.

31. The combination of a perfume carrier and a beaker according to claim 29, wherein said foil seal is peelably fastened to the mouth of said beaker, so that said foil may be removed before the perfume carrier is attached to an artificial flower.

32. The combination of perfume carrier and a beaker according to claim 29, wherein said foil seal is permanently fastened to the mouth of said beaker and it comprises of a material capable of being pierced by the protruding stem portion of an artificial flower.

33. A perfume carrier blank manufactured by the method of claim 2.

* * * * *